(12) United States Patent
Peratello et al.

(10) Patent No.: US 6,355,856 B2
(45) Date of Patent: *Mar. 12, 2002

(54) CATALYST BASED ON MOLYBDENUM AND ITS USE IN THE ISOMERIZATION OF N-PARAFFINS

(75) Inventors: Stefano Peratello, Besana in Brianza; Angela Carati, Zivido Si Giuliano Milise; Giuseppe Bellussi, Piacenza; Caterina Rizzo, Si Donato Milise, all of (IT)

(73) Assignees: Agip Petroli S.p.A., Rome; EniTechnologies S.p.A., San Donato Milanese, both of (IT)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/338,431

(22) Filed: Jun. 23, 1999

(30) Foreign Application Priority Data

Jul. 16, 1998 (IT) .......................................... MI98A1633

(51) Int. Cl.⁷ ............................ C07C 5/22; B01J 21/08; B01J 23/28
(52) U.S. Cl. ..................... 585/750; 585/751; 585/750; 502/255; 502/232; 502/233; 502/321
(58) Field of Search .................................. 502/321, 232, 502/233, 255; 585/750, 751

(56) References Cited

U.S. PATENT DOCUMENTS

| | | | |
|---|---|---|---|
| 3,108,974 A | | 10/1963 | Carr |
| 4,028,273 A | * | 6/1977 | O'Hara et al. ............... 252/432 |
| 4,705,771 A | | 11/1987 | Spencer |
| 4,810,363 A | | 3/1989 | Van Den Berg |
| 4,885,427 A | * | 12/1989 | Reichmann ................. 585/480 |
| 5,081,267 A | | 1/1992 | Rameswaran et al. |
| 5,498,811 A | | 3/1996 | Perego et al. |
| 5,578,744 A | * | 11/1996 | Carati et al. ................. 585/530 |
| 5,625,108 A | | 4/1997 | Perego et al. |
| 5,888,466 A | | 3/1999 | Perego et al. |
| 6,037,303 A | * | 3/2000 | Peratello et al. ............ 502/217 |

\* cited by examiner

*Primary Examiner*—Bekir L. Yildirim
(74) *Attorney, Agent, or Firm*—Oblon, Spivak, McClelland, Maier & Neustadt, P.C.

(57) ABSTRACT

Catalyst based on molibden and silicon having a surface area ranging from 20 to 400 m²/g and a molar ratio Mo/Si>0.2 obtainable with a process which comprises:

a) dissolving a soluble molibden salt in an aqueous solution containing at least one basic compound selected from ammonium hydroxides having general formula (I):

$$R_1R_2R_3R_4N^+OH^- \qquad (I)$$

b) adding to the solution of step (a) at least one compound of silicon capable of hydrolyzing to $SiO_2$;

c) gelifying and calcining the gel obtained.

9 Claims, No Drawings

CATALYST BASED ON MOLYBDENUM AND ITS USE IN THE ISOMERIZATION OF N-PARAFFINS

BACKGROUND OF THE INVENTION

1. Field of the Invention

The present invention relates to a catalyst based on molybdenum and its use in the isomerization of n-paraffins.

2. Description of the Background

More specifically, the present invention relates to a catalyst based on molibden and silicon and its use in the isomerization reaction of n-paraffins with a number of carbon atoms higher than or equal to 5, preferably between 5 and 40.

The use of catalysts based on molibden for the isomerization of n-paraffins is known in literature. In particular, as described in "Proceeding of the 10th International Congress on Catalysis, Budapest, 1992, 955, the catalytic activity of these materials is linked to the formation of molibden carbides or oxycarbides which, with respect to the starting oxide, have a higher surface area which goes from about 4 $m^2/g$ ($MoO_3$ at 99.95% of purity) to values which can reach up to about 200 $m^2/g$.

The passage from molybdenum oxide to the catalyst is laborious and can be achieved in various ways, as illustrated hereunder.

The "Journal of Solid State Chemistry", 59, 1985, 332 and 348, describes attacking molybdenum oxide with a mixture of ammonia/hydrogen at 880° C. to obtain the corresponding nitride which is then transformed into carbide by treatment with methane/hydrogen at 900° C. The carbides obtained with this method have a surface area of 140–180 $m^2/g$.

Another method is described in "Journal of Catalysis", 106, 1987, 125. According to this method, the molybdenum oxide is treated with a stream of methane/hydrogen at an increasing temperature.

In "Journal of Catalysis" 112, 1988, 44, the oxide can be previously impregnated with 0.25% by weight of platinum that acts as carburization catalyst, which takes place at an increasing temperature up to 700° C. The end solids have an area of about 200 $m^2/g$.

Alternatively, according to what is described in "Journal of Catalysis" 117, 1989, 371, the molybdenum oxide can be reduced with hydrogen to the metal phase which is then carburized with CO at 100° C. Or, the carburation reaction can be carried out using vapours of $MoO_3$ on activated carbon obtaining materials with a surface area of 100–200 $m^2/g$, as described in European patent 396 475.

The synthesis in situ of molybdenum oxycarbides has recently been described, starting from $MoO_3$ treated at a low temperature (350° C.) in a stream of hydrogen/n-octane for 24 hours ("Catalysis Today", 35, 1997, 51).

The Applicant has now found a new catalytic structure based on molybdenum oxide and silica which can be used as such in the isomerization reaction of n-paraffins raffins without requiring particular pretreatments.

The present invention therefore relates to a catalyst based on molybdenum and silicon having a surface area ranging from 20 to 400 $m^2/g$ and a molar ratio Mo/Si>0.2.

SUMMARY OF THE INVENTION

A further object of the present invention relates to a catalyst based on molybdenum and silicon prepared by a process comprising:

a) dissolving a soluble molybdenum salt in an aqueous solution containing at least one basic compound selected from ammonium hydroxides having general formula (I):

$$R_1R_2R_3R_4N^+OH^- \qquad (I)$$

wherein the groups $R_1$–$R_4$, the same or different, represent aliphatic groups containing from 1 to 7 carbon atoms;

b) adding to the solution of step (a) at least one compound of silicon capable of hydrolyzing to $SiO_2$ in such quantities as to give a molar ratio Mo/Si greater than 0.2 and, optionally, an aliphatic alcohol;

c) gelling the mixture thus obtained and calcining the gel obtained in air at a temperature ranging from 500 to 600° C.

DESCRIPTION OF THE PREFERRED EMBODIMENTS

Any molybdenum salt soluble in water or in a basic environment can be used in the preparation process of the catalyst of the present invention. Practical examples are halogenated derivatives of molybdenum, for example, having the formula $MoO_2X_2$ wherein X represents a halogen such as chlorine, bromine or fluorine, or having the formula $MoOX_4$, wherein X represents a chlorine or fluorine atom, molibdic anhydride, molibdic acid and ammonium tetrahydrate heptamolybdate.

The molybdenum salt is dissolved in an aqueous solution of the basic compound having general formula (I). Of these basic products tetrapropylammonium hydroxide is preferred.

When the molybdenum salt has dissolved, the hydrolyzable silicon compound, optionally diluted with an alcohol, is added to the solution. The preferred silicon compound according to the present invention is silicon tetra-alkyl orthosilicate in which the alkyl group contains from 1 to 4 carbon atoms such as, for example, tetra-ethyl orthosilicate.

The alcohol is preferably selected from aliphatic alcohols, in particular $C_2$–$C_6$ alkyl monoalcohols.

The preparation of the gelifiable solution based on molybdenum, steps (a) and (b), substantially takes place at room temperature, dosing the reaction ingredients so that they respect the following molar ratios:
Mo/Si greater than 0.2;
$OH^-$/(Si+Mo) greater than 0.1;
$H_2O$/(Si+Mo) greater than 5;
Alcohol/$H_2O$ between 0 and 20.

More specifically, the ingredients are preferably dosed so as to obtain the following molar ratios:
Mo/Si between 1 and 100;
$OH^-$/(Si+Mo) between 0.2 and 5;
$H_2O$/(Si+Mo) between 10 and 100;
Alcohol/$H_2O$ between 0.5 and 2.

When the reaction mixture has been prepared, the gelation phase begins. This can be carried out at room temperature or at a temperature ranging from room values to 100° C.

The gelation may require times ranging from a few minutes to several hours (even up to 100) and can take place both under stirring and under static conditions. It leads to the formation of a homogeneous gel which may be transparent or opaque. The formation of supernatant phases has never been observed.

At the end of the gelation phase, the gel produced is dried at 100° C. for a few hours and is then calcined in air at 500–600° C.

The catalyst of the present invention appears as a solid having a surface area ranging from 20 to 400 m²/g, a pore volume ranging from 0.5 to 1 cm³/g, with distribution centred in the mesopore region.

The catalyst of the present invention is useful in the isomerization reaction of n-paraffins, in particular n-paraffins with a number of carbon atoms higher than or equal to 5, preferably between 5 and 40.

A further object of the present invention therefore relates to a process for the isomerization of n-paraffins characterized in that the isomerization reaction is carried out in the presence of a catalyst prepared by a process comprising:

a) dissolving a soluble molybdenum salt in an aqueous solution containing at least one basic compound selected from ammonium hydroxides having general formula (I):

$$R_1R_2R_3R_4N^+OH^- \quad (I)$$

wherein the groups $R_1$–$R_4$, the same or different, represent aliphatic groups containing from 1 to 7 carbon atoms;

b) adding to the solution of step (a) at least one compound of silicon capable of hydrolyzing to $SiO_2$ and, optionally, an aliphatic alcohol;

c) gelling the mixture thus obtained and calcining the gel obtained in air at a temperature ranging from 500 to 600° C.

The preferred catalyst for the isomerization reaction is the catalyst based on molybdenum and silicon having a surface area ranging from 20 to 400 m²/g and a molar ratio Mo/Si>0.2.

The isomerization of n-paraffins can be carried out in any type of reactor. It is preferable, however, to operate with fixed-bed or fluid-bed reactors, either in continuous or batch.

The isomerization reaction is carried out in the presence of hydrogen, at a temperature ranging from 200 to 550° C., preferably between 250 and 450° C., and at a hydrogen pressure ranging from atmospheric pressure to 10 MPa, preferably from 2 to 6 MPa.

Some illustrative but non-limiting examples are provided for a better understanding of the present invention and for its embodiment.

EXAMPLE 1

20 g of ammonium tetrahydrate heptamolybdate (EMA) are dissolved in 200 g of an aqueous solution of tetrapropylammonium hydroxide (TPAOH) at 10% by weight. A solution consisting of 53 g of tetra-ethyl orthosilicate (TES) and 160 g of ethanol are then added.

After about 7 minutes the presence of a homogeneous opaque gel is observed, without separation of supernatant phases. It is left to rest at room temperature for a night and is then dried at 100° C. for 15 hours and calcined at 550° C. for 6 hours in air.

The solid obtained has the following composition (weight %): $MoO_3$=50%; $SiO_2$=50%. It has a surface area of 161 m²/g, a pore volume of 0.53 cm³/g, an average pore diameter of 126 nm, calculated from the desorption isotherm.

EXAMPLE 2

20 g of EMA are dissolved in 200 g of an aqueous solution of TPAOH at 15% by weight. A solution consisting of 53 g of TES and 160 g of ethanol are then added.

After about 7 minutes the presence of a homogeneous opaque gel is observed, without separation of supernatant phases. It is left to rest at room temperature for a night and is then dried at 100° C. for 15 hours and calcined at 550° C. for 6 hours in air.

The solid obtained has the following composition (weight %): $MoO_3$=50%; $SiO_2$=50%. It has a surface area of 116 m²/g, a pore volume of 0.45 cm³/g, an average pore diameter of 204 nm, calculated from the desorption isotherm.

EXAMPLE 3

20 g of EMA are dissolved in 200 g of an aqueous solution of TPAOH at 30% by weight. A solution consisting of 53 g of TES and 160 g of ethanol are then added.

After about 15 hours at room temperature the formation of a limpid gel is observed which is dried at 100° C. for 22 hours and calcined at 550° C. for 6 hours in air.

The solid obtained has the following composition (weight %): $MoO_3$=50%; $SiO_2$=50%. It has a surface area of 48 m²/g, a pore volume of 0.11 cm³/g, an average pore diameter of 72 nm, calculated from the desorption isotherm.

EXAMPLE 4

The synthesis described in example 3 is repeated without alcohol.

The solid obtained has the following composition (weight %): $MoO_3$=50%; $SiO_2$=50%. It has a surface area of 53 m²/g, a pore volume of 0.08 cm³/g.

EXAMPLE 5

20 g of EMA are dissolved in 200 g of an aqueous solution of TPAOH at 35% by weight. A solution consisting of 53 g of TES and 160 g of ethanol are then added.

After about 60 hours at room temperature the formation of a limpid gel is observed which is dried at 100° C. for 15 hours and calcined at 550° C. for 6 hours in air.

The solid obtained has the following composition (weight %): $MoO_3$=50%; $SiO_2$=50%. It has a surface area of 54 m²/g, a pore volume of 0.09 cm³/g, an average pore diameter of 38 nm, calculated from the desorption isotherm.

EXAMPLE 6

20 g of EMA are dissolved in 150 g of an aqueous solution of TPAOH at 40% by weight. A solution consisting of 53 g of TES and 160 g of ethanol are then added.

After about 7 hours at room temperature the formation of a limpid gel is observed which is dried at 100° C. for 15 hours and calcined at 550° C. for 6 hours in air.

The solid obtained has the following composition (weight %): $MoO_3$=50%; $SiO_2$=50%. It has a surface area of 50 m²/g, a pore volume of 0.08 cm³/g.

EXAMPLE 7

20 g of EMA are dissolved in 150 g of an aqueous solution of TPAOH at 40% by weight. A solution consisting of 53 g of TES and 230 g of ethanol are then added.

After about 60 hours at room temperature the formation of a limpid gel is observed which is dried at 100° C. for 15 hours and calcined at 550° C. for 6 hours in air.

The solid obtained has the following composition (weight %): $MoO_3$=50%; $SiO_2$=50%.

EXAMPLE 8

20 g of EMA are dissolved in 150 g of an aqueous solution of TPAOH at 40% by weight. A solution consisting of 24 g of TES and 160 g of ethanol are then added.

After about 24 hours at room temperature the formation of a limpid gel is observed which is dried at 100° C. for 15 hours and calcined at 550° C. for 6 hours in air.

The solid obtained has the following composition (weight %): $MoO_3$=68.8%; $SiO_2$=31.2%.

EXAMPLE 9

20 g of EMA are dissolved in 150 g of an aqueous solution of TPAOH at 40% by weight. A solution consisting of 5 g of TES and 160 g of ethanol are then added.

After about 24 hours at room temperature the formation of a limpid gel is observed which is dried at 100° C. for 15 hours and calcined at 550° C. for 6 hours in air.

The solid obtained has the following composition (weight %): $MoO_3$=91.4%; $SiO_2$=8.6%.

EXAMPLE 10

Comparative 20 g of EMA are dissolved in 230 g of an aqueous solution of $NH_4OH$ at 23% by weight. A solution consisting of 50 g of TES and 160 g of ethanol are then added.

A lactescent suspension is formed, which after about 16 hours at room temperature gives a white solid, without separation of a supernatant solution. The product obtained is dried at 100° C. for 15 hours and calcined at 550° C. for 6 hours in air.

The solid obtained has the following composition (weight %): $MoO_3$=51.5%; $SiO_2$=48.5%. The surface area is 4 $m^2/g$.

EXAMPLE 11

Comparative

Example 9 is repeated without TES. An end-solid is obtained consisting of 100% of molybdenum oxide. The surface area is 2 $m^2/g$.

As can be seen from comparative examples 10 and 11, the morphological characteristics of materials according to the present invention are linked to the contemporaneous presence of tetralkyl ammonium hydroxide and the silicon compound in the reagent mixture.

EXAMPLE 12

The catalyst described in example 3 was evaluated in the hydroisomerization reaction of n-heptane. The reactor is a tubular, fixed-bed reactor, having an internal diameter of 1 cm and a length of 35 cm. 5 g of catalyst sieved to 20–40 mesh, were charged into the reactor.

The isomerization reaction was initiated by bringing the reactor to a temperature of about 100° C. in a stream of nitrogen, a mixture of hydrogen/n-heptane was then fed in a molar ratio 30/1 and the temperature was raised to 350° C. over a period of about 1 hour.

The reaction conditions are the following:

T=350° C.;
P=2 MPa;
$H_2/n$-$C_7$=30 mol/mol;
WHSV=1 $h^{-1}$.

WHSV (Weight Hourly Space Velocity) refers to the n-heptane and is expressed as grams of n-heptane per grams of catalyst per hour.

The isomerization reaction was carried out for 50 hours, observing that conversion and selectivity remain constant within this time period. In particular, the conversion of n-heptane was 79.5% with a selectivity to iso-$C_7$ of 97.4%.

EXAMPLE 13

The catalyst described in example 2 was evaluated in the hydroisomerization reaction of n-hexadecane. The reactor is a tubular, fixed-bed reactor, having an internal diameter of 1.2 cm and a length of 45 cm. 9 g of catalyst sieved to 20–40 mesh, were charged into the reactor.

The isomerization reaction was initiated by feeding a mixture of hydrogen/n-hexadecane in a molar ratio 32/1 and the temperature was raised to 350° C. over a period of about 2 hours.

The reaction conditions are the following:

T=350° C.;
P=5 MPa;
$H_2/n$-$C_{16}$=32 mol/mol;
WHSV=1 $h^{-1}$.

The isomerization reaction was carried out for 60 hours, observing that conversion and selectivity remain constant within this time period. In particular, the conversion of n-hexadecane was 94% with a selectivity to iso-$C_{16}$ of 75%.

EXAMPLE 14

Comparative

The isomerization reaction described in example 12 was repeated using the catalyst of comparative example 11.

The following table indicates the test results in terms of conversion and selectivity.

TABLE

| TIME (h) | CONVERSION N-HEPTANE % | SELECTIVITY ISO-$C_7$ % | SELECTIVITY CRACKING % |
|---|---|---|---|
| 2 | 17 | 96 | 4 |
| 20 | 50 | 95.7 | 4.3 |
| 40 | 43 | 91.3 | 8.7 |
| 68 | 44 | 82.2 | 17.8 |

What is claimed is:

1. A molybdenum oxide/silica catalyst prepared by a process, comprising:

i) dissolving a soluble molybdenum salt in an aqueous solution containing at least one basic compound selected from the group consisting of ammonium hydroxides having formula (I):

$$R_1R_2R_3R_4N^+OH^- \quad (I)$$

wherein groups $R_1$–$R_4$, the same or different, represent aliphatic groups containing from 1 to 7 carbon atoms;

ii) adding to the solution of step (i) at least one compound of silicon capable of hydrolyzing to $SiO_2$ in such quantities as to give a molar ratio Mo/Si greater than 0.2 and, optionally, an aliphatic alcohol; and iii) gelling the mixture thus obtained and calcining the gel obtained in air at a temperature ranging from 500 to 600° C., thereby preparing a catalyst having a surface area of 20 to 400 $m^2/g$ and a molar ratio of Mo/Si>0.2.

2. The catalyst according to claim 1, wherein the soluble molybdenum salt selected from the group consisting of halogenated derivatives of molybdenum have the formula $MoO_2X_2$ wherein X represents chlorine, bromine or fluorine, or has the formula $MoOX_4$ wherein X represents a chlorine or fluorine atom; molybdic anhydride, molybdic acid and ammonium tetrahyate heptamolybdate.

3. The catalyst according to claim 1, wherein the silicon compound is silicon tetra-alkyl orthosilicate in which the alkyl group contains from 1 to 4 carbon atoms.

4. The catalyst according to claim 1, wherein the gelifiable solution prepared according to steps (i) and (ii) has the following molar composition:

Mo/Si greater than 0.2;

$OH^-$/(Si+Mo) greater than 0.1;

$H_2O$/(Si+Mo) greater than 5;

alcohol/$H_2O$ ranging from 0 to 20.

5. The catalyst according to claim 1, wherein the gelation phase is carried out at room temperature or at a temperature ranging from room temperature to 100° C.

6. The catalyst according to claim 1, having a surface area ranging from 20 to 400 $m^2$/g, a pore volume ranging from 0.05 to 1 $cm^3$/g, with distribution centered in the mesopore region.

7. A process for the isomerization of n-paraffins in an isomerization reaction conducted by contacting the paraffin with a molybdenum oxide/silica catalyst prepared by a process, comprising:

i) dissolving a soluble molybdenum salt in an aqueous solution containing at least one basic compound selected from the group consisting of amnmonium hydroxides having formula (I):

$$R_1R_2R_3R_4N^+OH^- \qquad (I)$$

wherein groups $R_1$–$R_4$, the same or different, represent aliphatic groups containing from 1 to 7 carbon atoms;

ii) adding to the solution of step (i) at least one compound of silicon capable of hydrolyzing to $SiO_2$ in such quantities as to give a molar ratio Mo/Si greater than 0.2 and, optionally, an aliphatic alcohol; and iii) gelling the mixture thus obtained and calcining the gel obtained in air at a temperature ranging from 500 to 600° C., thereby preparing a catalyst having a surface area of 20 to 400 $m^2$/g and a molar ratio of Mo/Si>0.2.

8. The process according to claim 7, wherein the isomerization reaction is conducted in the presence of hydrogen, at a temperature ranging from 200 to 550° C. and at a hydrogen pressure ranging from atmospheric pressure to 10 MPa.

9. The process according to claim 7, wherein the n-paraffins have a number of carbon atoms equal to or higher than 5.

* * * * *

UNITED STATES PATENT AND TRADEMARK OFFICE
CERTIFICATE OF CORRECTION

PATENT NO. : 6,355,856 B2
DATED : March 12, 2002
INVENTOR(S) : Peratello et al.

It is certified that error appears in the above-identified patent and that said Letters Patent is hereby corrected as shown below:

<u>Title page,</u>
Item [75], the Inventors' city of residence should read:

-- [75] Inventors: Stefano Peratello, Besana in Brianza; Angela Carati, Zivido S. Giuliano Mil.se; Giuseppe Bellussi, Piacenza; Caterina Rizzo, S. Donato Mil.se, all of (IT) --

Item [73], the Assignees' information should read:

-- [73] Assignees: Agip Petroli S.p.A., Rome; EniTecnologie S.p.A., San Donato Milanese, both of (IT) --

Signed and Sealed this

First Day of October, 2002

*Attest:*

JAMES E. ROGAN
*Attesting Officer*     *Director of the United States Patent and Trademark Office*